United States Patent [19]

Crocker et al.

[11] Patent Number: 5,750,741

[45] Date of Patent: May 12, 1998

[54] PREPARATION OF OXIRANE COMPOUNDS WITH TITANASILSESQUIOXANE CATALYSTS

[75] Inventors: Mark Crocker; Rudolf Henri Max Herold, both of Amsterdam, Netherlands

[73] Assignee: Shell Oil Company, Houston, Tex.

[21] Appl. No.: 783,965

[22] Filed: Jan. 15, 1997

[51] Int. Cl.$^6$ .................................. C07D 301/14
[52] U.S. Cl. ........................... 549/525; 549/523
[58] Field of Search ........................ 549/525, 523

[56] References Cited

U.S. PATENT DOCUMENTS

| | | | |
|---|---|---|---|
| 5,374,747 | 12/1994 | Saxton et al. | 549/531 |
| 5,466,835 | 11/1995 | Nemeth et al. | 549/531 |

OTHER PUBLICATIONS

Buys, I.E. et al, 'Models of Surface–Confined metallocene Derivatives.' J. Mol. Catal., 1994, 86, pp. 309–318.

Winkhofer, N. et al, 'Stable Silanetriols as Building Blocks for the Synthesis of Titanasilasesquioxanes–Model Compounds for Titanium–Doped Zeolites.' Angew. Chem. Int. Ed. Engl., 1994, 33(13), pp. 1352–1354.

Feher, F.J. et al, 'Silasesquioxanes as Ligands in Inorganic and Organometallic Chemistry.' Polyhedron, 1995, 14(22), pp. 3239–3253.

*Primary Examiner*—C. Warren Ivy
*Assistant Examiner*—Garth M. Dahlen
*Attorney, Agent, or Firm*—Dennis V. Carmen

[57] ABSTRACT

A process for the preparation of an oxirane compound by reacting an olefinically unsaturated hydrocarbon with an organic hydroperoxide, in the presence of a catalyst comprising a titanasilsesquioxane of the general formula $TiLR_7Si_7O_{12}$ and the structural formula

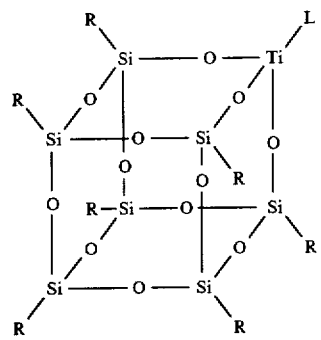

wherein R is chosen from the group of cyclopentyl, cyclohexyl and cycloheptyl and L is chosen from the group of alkyl, cycloalkyl, alkylaryl, alkoxy, aryloxy, siloxy, amido and OH.

11 Claims, No Drawings

PREPARATION OF OXIRANE COMPOUNDS WITH TITANASILSESQUIOXANE CATALYSTS

FIELD OF THE INVENTION

The present invention relates to a process wherein an olefinically unsaturated hydrocarbon ("olefin") is reacted with an organic hydroperoxide to produce an epoxide (oxirane compound) and an alcohol, in the presence of a catalyst comprising titanium and silicon.

BACKGROUND OF THE INVENTION

This well-known type of reaction is of special commercial importance for the epoxidation of substituted or unsubstituted alkenes such as propene (to propene oxide), allyl chloride (to epichlorohydrine) and octene (to octene oxide) —whereby the organic hydroperoxide used may be aliphatic such as tertiary butyl hydroperoxide, or aromatic such as ethylbenzene hydroperoxide.

A variety of homogeneous and heterogeneous catalysts has been employed for the reaction of olefins with organic hydroperoxides.

U.S. Pat. No. 3,350,422 and U.S. Pat. No. 3,351,635 disclose the use of solutions of transition metal compounds (V, Mo, W, Ti, Nb, Ta, Re, Se, Zr, Te and U), as homogeneous catalysts. S. Coleman-Kamula and E. Duim-Koolstra in J. organomet. Chem. 246 1983 53–56 disclose the use of a solution of molybdenyl acetylacetate as a homogeneous catalyst.

U.S. Pat. No. 4,367,342 discloses the use of inorganic oxygen compounds of silicon in chemical composition with at least 0.1 wt % of an oxide or hydroxide of titanium, as heterogeneous catalysts. And EP-B-0 345 856 discloses a titanium/silica heterogeneous catalyst which is obtainable by impregnating the silicon compound with a stream of gaseous titanium tetrachloride, followed by calcination and hydrolysis steps.

The above catalysts are effective in the epoxidation of the lower alkenes such as propene, but there still exists a need for more effective (active as well as selective) general purpose olefin epoxidation catalysts.

Incompletely condensed silsesquioxanes of the general formula $R_7Si_7O_9(OH)_3$ have been proposed as models for silica surfaces. F. J. Feher et al in J. Am. Chem. Soc. 111 1989 1741–1748 describe the hydrolytic condensation of cyclohexyltrichlorosilane to the incompletely condensed silsesquioxane compound (c—$C_6H_{11}$)$_7$$Si_7$$O_9$(OH)$_3$, the structure of which has great similarity with the crystalline forms of silica, beta-cristobalite and tridymite. In organometallics 10 1991 2526–2528 Feher et al. disclose that the similar condensation reactions of cyclopentyl (c—$C_5H_9$) and of cycloheptyl (c—$C_7H_{13}$) trichlorosilane are much quicker than that of cyclohexyltrichlorosilane, which latter reaction is inconveniently slow.

It is also known that the three neighboring OH groups in the above silsesquioxane compounds can be further reacted with a transition metal compound to form the corresponding metallasilsesquioxane. I. E. Buys et al. in J. Mol. Catalysis 86 1994 309–318 disclose the reaction of titanium, zirconium or hafnium compounds, such as cyclopentadienyl titanium trichloride CpTiCl$_3$ which reacts with the silsesquioxane (c—$C_6H_{11}$)$_7$$Si_7$$O_9$(OH)$_3$ to form the corresponding metallasilsesquioxane (c—$C_6H_{11}$)$_7$$Si_7$$O_{12}$TiCp and HCl. Finally, N. Wikorfer et al. in Angew. Chem. Int. Ed. Engl. 33 1994 1352–1353 suggest but do not show that similar titanasilsesquioxanes, containing more than one titanium atom per molecule, may be effective as catalysts.

It has now been found that certain titanasilsesquioxanes are particularly effective in the production of oxirane compounds from olefinically unsaturated hydrocarbons and organic hydroperoxides.

SUMMARY OF THE INVENTION

The present invention concerns a process for the preparation of an oxirane compound by reacting an olefinically unsaturated hydrocarbon with an organic hydroperoxide, in the presence of a catalyst comprising a titanasilsesquioxane of the general formula $TiLR_7Si_7O_{12}$ and the structural formula

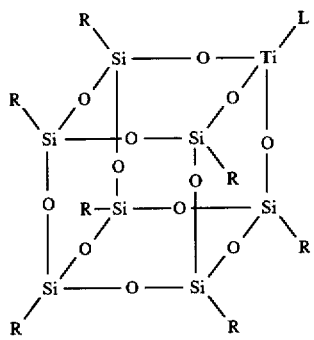

wherein R is chosen from the group of cyclopentyl, cyclohexyl and cycloheptyl and L is chosen from the group of alkyl, cycloalkyl, alkylaryl, alkoxy, aryloxy, siloxy, amido and OH.

Preferably, L is chosen from the group of phenoxy, isopropoxy, benzyl, trimethylsiloxy and dimethyl amido.

DETAILED DESCRIPTION OF THE INVENTION

The incompletely condensed silsesquioxanes $R_7Si_7O_9(OH)_3$ are generally prepared by addition of excess water to a vigorously stirred solution of the appropriate trichlorosilane, $RSiCl_3$, in an organic solvent. The solvent employed is preferably one which is miscible with water and in which the product silsesquioxane is insoluble or only slightly soluble. Suitable solvents include acetone, acetonitrile, dimethylformamide and dimethylsulfoxide. The concentration of the trichlorosilane is typically in the range of 0.01–1.0M, and most preferably in the range of 0.1–0.6M. The volume of water added to the dissolved trichlorosilane is such that the final concentration of water in the reaction mixture is between 1 and 60 vol %, and preferably between 5 and 40 vol %. The reaction mixture can be left to stand at room temperature and atmospheric pressure, in which case the crude silsesquioxane product precipitates out of solution during the following weeks. In the case of the cyclopentyl- and cycloheptyl- substituted trichlorosilanes, refluxing the reaction mixture accelerates the formation of the silsesquioxane product (as described in the 1991 Feher et al. publication), such that product yields of up to 60% can be obtained after a few days.

Isolation of the silsesquioxane product is achieved by filtering off the solid from the reaction mixture. Before being used for the preparation of titanasilsesquioxanes, the incompletely condensed silsesquioxanes are preferably purified, using methods standard to preparative organic chemistry. Typically the incompletely condensed silsesquioxane is extracted into a basic solvent such as pyridine or triethylamine and separated from insoluble material by filtration. The weight of solvent used is generally between 5 and 40 times that of the crude silsesquioxane. The solvent is then removed, either under reduced pressure, or by reaction with a slight excess of aqueous mineral acid. In the latter case, the resulting pyridinium or organoammonium salt is removed by washing with water. If the pyridine or amine solvent is removed under reduced pressure, then the last traces of solvent are preferably removed from the solid by briefly washing the silsesquioxane with dilute aqueous mineral acid (preferably not stronger than 1M), followed by water. After drying, the solid is briefly washed with pentane (using between 0.5 and 5 ml pentane/g product), to afford a product of generally acceptable purity (typically >95%). Material of >99% purity can be obtained by recrystallizing the product from a solvent in which it is quite soluble, such as hot diethyl ether.

The titanasilsesquioxanes $TiLR_7Si_7O_{12}$ according to the invention are typically prepared by stirring a homoleptic titanium complex, $TiM_4$ (M being at least one group L and at most three halogen atoms-see the Buys et al. publication), with a stoichiometric amount of the appropriate incompletely condensed silsesquioxane $R_7Si_7O_9(OH)_3$ in an aprotic organic solvent in which the reactants are sufficiently soluble. Suitable solvents include pentane, toluene, diethyl ether, THF and dichloromethane. The reaction is typically performed under an inert gas (e.g., nitrogen or argon) at room temperature and at about atmospheric pressure, and is generally complete within a few minutes. The concentration of the reactants is not of prime importance, but convenient concentrations are in the region of 0.01–0.1M for each reactant when R is cyclohexyl, and 0.001–0.005M for each reactant when R is cyclopentyl or cycloheptyl.

Isolation of the titanasilsesquioxane product is most conveniently accomplished by removing the volatile material present (i.e. solvent and reaction co-product MH) under reduced pressure. Analytically pure material is obtained by precipitating the titanasilsesquioxane from solution by adding a polar, aprotic solvent in which the complex is insoluble (e.g., acetonitrile). If the complex is to be used directly as a catalyst, then it is most conveniently generated in situ and used without further purification.

Once prepared, a titanasilsesquioxane can be modified by exchanging its ligand $L^1$ (alkyl, cycloalkyl, arylalkyl or amido) for another appropriate ligand $L^2$, e.g. by adding a stoichiometric amount of a protic species ($L^2H$) such as an alcohol, arylalcohol, silanol or water, to the titanasilsesquioxane:

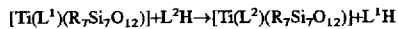

$$[Ti(L^1)(R_7Si_7O_{12})] + L^2H \rightarrow [Ti(L^2)(R_7Si_7O_{12})] + L^1H$$

The reaction conditions are similar to those for preparing the titanasilsesquioxanes. If desired the new ($L^2$) titanasilsesquioxane can be isolated using the procedure described above, but it is also convenient to prepare the $L^2$ titanasilsesquioxane in situ and use it as a catalyst without purification.

The titanasilsesquioxanes according to the invention are generally soluble in apolar organic solvents such as pentane, diethyl ether and toluene, and insoluble in polar organic solvents such as acetonitril, dimethyl formamide, dimethyl sulfoxide and methanol. The reagents, olefins as well as organic hydroperoxides, are soluble in both polar and apolar organic solvents. Therefore, the process according to the invention can be performed in a homogeneous system when the catalyst as well as the reagents are dissolved in an apolar organic solvent, or in a heterogeneous system whereby only the reagents are dissolved in a polar organic solvent. In the latter case the titanasilsesquioxane catalyst may be used as such in a slurry, but preferably it is impregnated on an inert inorganic carrier material, having a specific surface area of at least 10 m² per gram and a pore volume of at least 0.1 ml per gram. The inert carrier should preferably not contain free acid or basic groups. Silylated silica, silicon carbide and activated coal are preferred inert carriers.

The titanasilsesquioxanes are preferably immobilized on an appropriate support using the pore volume impregnation (PVI) technique. A concentrated solution of the titanasilsesquioxane is added to the carrier, the volume of liquid employed being approximately equal to the total pore volume of the support. Suitable solvents are those in which the titanium complex is very soluble, such as aromatic hydrocarbons, alkanes and ethers. After impregnation the solid is agitated so as to ensure efficient spreading of the liquid on the carrier, after which the solvent is removed (either by heating or by drying under reduced pressure). The loading of titanium complex can be controlled as desired by altering the concentration of the solution used for the impregnation. Desirable titanasilsesquioxane loadings are typically in the range of 5–60 wt %, and preferably in the range of 10–25 wt %, depending on the surface area of the support.

The olefinically unsaturated hydrocarbon reactant may in principle be any organic compound having at least one olefinic double bond. The compound may be acyclic, monocyclic, bicyclic or polycyclic and it may be monoolefinic, diolefinic or polyolefinic. If there are more than one olefinic linkages, these may either be conjugated or nonconjugated. Generally preferred are olefinic compounds having from 2 to 60 carbon atoms. Although substituents, which should preferably be relatively stable, may be present, acyclic monoolefinic hydrocarbons having from 2 to 10 carbon atoms are of particular interest. Such hydrocarbons include, e.g., ethylene, propylene, isobutylene, hexene-3, octene-1 and decene-1. Butadiene may be mentioned as an example of a suitable diolefinic hydrocarbon. Substituents, if present, may, e.g., be halogen atoms or comprise atoms of oxygen, sulphur and nitrogen together with atoms of hydrogen and/or carbon. Of particular interest are olefinically unsaturated alcohols, and halogen-substituted olefinically unsaturated hydrocarbons, including, e.g., allyl alcohol, crotyl alcohol and allyl chloride. Particularly preferred are alkenes having from 3 to 40 carbon atoms, which may or may not be substituted with a hydroxy or a halogen atom.

The organic hydroperoxide reactant may generally be any organic compound represented by the general formula R—O—O—H, in which R is a monovalent hydrocarbyl group, which will react with the olefinic compound to form an oxirane compound and a compound R—OH. Preferably, the group R has from 3 to 20 carbon atoms. Most preferably, it is a hydrocarbyl group, in particular a secondary or tertiary alkyl or aralkyl group, having from 3 to 10 carbon atoms. Especially preferred among these groups are the tertiary alkyl and secondary or tertiary aralkyl groups, including, e.g., tertiary butyl, tertiary pentyl, cyclopentyl, 1-phenylethyl-1, 2-phenylpropyl-2 and the various tetralinyl radicals which originate by elimination of a hydrogen atom from the aliphatic side-chain of the tetralin molecule.

Aralkyl hydroperoxide, wherein the hydroperoxy group is linked to that carbon atom of an alkyl side-chain which is attached directly to an aromatic ring, including 1-phenylethyl-1-hydroperoxide and 2-phenylpropyl-2-hydroperoxide, are often called after the corresponding hydrocarbons, e.g. ethyl benzene hydroperoxide and cumene hydroperoxide. Preferred organic hydroperoxides are ethylbenzene hydroperoxide (EBHP), cumene hydroperoxide and tertiary butyl hydroperoxide (TBHP).

The process according to the invention can be operated in batch, or in continuous operation.

The epoxidation reaction of the invention is generally conducted in the liquid phase using solvents and/or diluents which are liquid at the reaction temperature and pressure, and substantially inert to the reactants, the catalyst and the products. The presence of reactive materials such as water is desirably avoided. A substantial part of the solvent/diluent may consist of materials present in the organic hydroperoxide solution employed. An excess of the amount of olefinic reactant may also serve as a solvent together with the solvent introduced with the organic peroxide. The total amount of solvent may be up to 20 moles per mole of hydroperoxide.

The amount of titanasilsesquioxane used in a homogeneous reaction system will generally be in the range from 1 to $10^{-6}$, preferably from $10^{-3}$ to $10^{-5}$, mol of titanium (calculated as the oxide) per mol of the organic hydroperoxide to be reacted.

In a homogeneous reaction system the titanasilsesquioxane catalyst can be introduced into the reactor either as a solid, or more conveniently as a solution in an appropriate (preferably non-coordinating or weakly coordinating) apolar solvent such as an alkane, alkene (e.g. the reactant itself), toluene and dichloromethane.

If the titanasilsesquioxane catalyst is immobilized on a carrier, the solvent employed in the reaction must be one in which the titanasilsesquioxane is not soluble, such as acetonitrile, dimethylformamide and dimethylsulfoxide. The heterogeneous catalyst may be operated in a fixed-bed mode. If operated in a batch mode, it may be isolated by filtration at completion of the epoxidation reaction.

The epoxidation reaction generally is performed at moderate temperatures and pressures. The temperature typically is in the range from 0° to 200° C., the range from 25° to 200° C. being preferred. The precise pressure is not critical as long as it suffices to maintain the reaction mixture in liquid condition. Atmospheric pressure may be satisfactory. In general, pressures are suitable in the range from 100 to 10000 kPa.

At the conclusion of the reaction, the product mixture is separated and the products are recovered by conventional methods such as fractional distillation, selective extraction and filtration. The solvent, the catalyst and any unreacted olefin or hydroperoxide can be recycled.

In the process of the invention, the olefin reactant is converted to olefin oxide (oxirane compound). These products are materials of established utility and many of them are chemicals of commerce. For example, propylene oxide is formulated into useful polymers and copolymers.

The organic hydroperoxide reactant is converted to the corresponding alcohol, which can be recovered as a by-product of the process or reconverted to the hydroperoxide.

The following examples will illustrate the invention.

EXAMPLE 1

Preparation of Incompletely Condensed Silsesquioxanes.

1.1=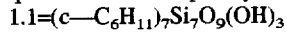

Distilled water (3.6 l) was added to a vigorously stirred solution of cyclohexyltrichlorosilane (c—$C_6H_{11}$)SiCl$_3$ (750 g, 3.5 mol) in acetone (14 l), after which stirring was stopped and the mixture left to stand in a stoppered flask at ambient temperature and atmospheric pressure for 6 months. After this time the solid present was isolated by filtration, the resulting filter-cake being broken up with a spatula and briefly stirred with pentane (200 ml). The slurry was filtered and the resulting solid washed with pentane until the solid was white in color. Drying overnight in a vacuum oven (60° C.) afforded 82 g of crude product. Extraction of the product with pyridine, followed by neutralization with aqueous HCl, filtration and crystallization from ether (as described in the 1989 Fehler et al. publication) afforded 33 g of the pure incompletely condensed silsesquioxane.

The pentane filtrate and washings from above were combined and volatile material removed on a rotary evaporator. The brown residue was dissolved in a minimum of acetone and added to the aqueous acetone which had earlier been filtered. The flask was re-stoppered and left to stand for a further year before the sequence of silsesquioxane isolation was repeated. After a period of 3 years the total yield of (c—$C_6H_{11}$)$_7$Si$_7$O$_9$(OH)$_3$ was 180 g.

1.2=(c—$C_5H_9$)$_7$Si$_7$O$_9$(OH)$_3$

Distilled water (350 ml) was added to a vigorously stirred solution of (c—$C_5H_9$)SiCl$_3$ (63 g, 0.31 mol) in acetone (1.2l), after which the mixture was refluxed for 72 h. The solid present was isolated by filtration and the resulting filter-cake was broken up with a spatula and briefly stirred with pentane (150 ml). The slurry was filtered and the resulting solid washed with pentane until the solid was white in color. Drying overnight in a vacuum oven (60° C.) afforded 24 g of crude product. Extraction of the product with pyridine, followed by neutralization with aqueous HCl, filtration and extraction into diethyl ether according to the method described in the 1991 Fehler et al. publication afforded the pure silsesquioxane in 44% yield.

EXAMPLE 2

Preparation of Titanasilsesquioxanes

All manipulations were performed under atmospheric pressure, under argon or nitrogen. Solvents were dried before use.

2.1=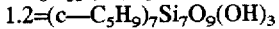

Diethyl ether (20 ml) was added to a solid mixture of Ti(CH$_2$Ph)$_4$ (0.500 g, 1.21 mmol) and the silsesquioxane (c—$C_6H_{11}$)$_7$Si$_7$O$_9$(OH)$_3$ (1.179 g, 1.21 mmol). The mixture was stirred at room temperature for 30 min. and the resulting solution filtered. Acetonitrile was then added dropwise to the filtrate to afford a precipitate of Ti(CH$_2$Ph){(c—$C_6H_{11}$)$_7$Si$_7$O$_{12}$}. The yellow solid was isolated by filtration, washed with acetonitrile (3×5 ml) and dried under vacuum (1.194 g, 89%).

The product was characterized on the basis of the following data: 1H NMR (C$_6$D$_6$, 250.1 MHz): 7.31–7.03 (m, 5 H, C$_6$H$_5$), 3.10 (s, 2 H, CH$_2$Ph), 2.20–0.97 (m, 77 H, c—C$_6$H$_{11}$). $^{13}$C NMR (C$_6$D$_6$, 100.6 MHz): 142.98 (s, ipso-Ph), 124.33 (s, Ph, other signals obscured by solvent), 81.17 (s, CH$_2$Ph), 27.77, 27.70, 27.60, 27.32, 27.30, 27.27, 27.21 (s, CH$_2$), 23.75, 23.72, 23.51 (s, 3:1:3 for CH). $^{29}$Si NMR (C$_6$D$_6$, 79.5 MHz): –65.55, –67.67, –68.73 (s, 3:1:3). Anal. Calcd for C$_{49}$H$_{84}$O$_{12}$Si$_7$Ti (found): C, 53.11 (52.79); H, 7.64 (7.68).

2.2=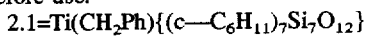

Addition of Ti(O$^i$Pr)$_4$ (0.62 g, 2.18 mmol) to a slurry of (c—$C_6H_{11}$)$_7$Si$_7$O$_9$(OH)$_3$ (2.050 g, 2.11 mmol) in diethyl ether (50 ml), followed by work-up as above, afforded Ti(O$^i$Pr){(c—$C_6H_{11}$) $_7$Si$_7$O$_{12}$ } as a white solid (2.240 g, 99%).

The product was characterized on the basis of the following data: $^1$H NMR (C$_6$D$_6$, 250.1 MHz): 4.41 (septet, 1 H, CH(CH$_3$)$_2$, J=6.1 Hz), 2.15–1.00 (m, 77 H, c—C$_6$H$_{11}$), 1.20 (d, 6 H, CH(CH$_3$)$_2$, J=6.1 Hz). $^{13}$C NMR (C$_6$D$_6$, 100.6 MHz): 80.09 (s, CH(CH$_3$)$_2$), 27.83, 27.81, 27.48, 27.44, 27.33, 27.28, 27.22 (s, CH$_2$), 25.80 (s, CH$_3$), 23.91, 23.85, 23.78 (s, 3:1:3 for CH). $^{29}$Si NMR (C$_6$D$_6$, 79.5 MHz): −64.75, −66.68, −67.67 (s, 3:1:3). Anal. Calcd for C$_{45}$H$_{84}$O$_{13}$Si$_7$Ti (found): C, 50.16 (49.93); H, 7.86 (7.70).

2.3=Ti(CH$_2$Ph){(c—C$_5$H$_9$)$_7$Si$_7$O$_{12}$}

A solution of [Ti(CH$_2$Ph)$_4$] (0.919 g, 2.23 mmol) in diethyl ether (20 ml) was added dropwise to a vigorously stirred suspension of the silsesquioxane (c—C$_5$H$_9$)$_7$Si$_7$O$_9$(OH)$_3$ (1.950 g, 2.23 mmol) in ether (100 ml). The resulting deep yellow solution was stirred for 2 h. The volume of solvent was then reduced under vacuum (to ca. 15 ml) and acetonitrile (15 ml) added to afford Ti(CH$_2$Ph){(c—C$_5$H$_9$)$_7$Si$_7$O$_{12}$} as a yellow precipitate. The solid was isolated by filtration, washed with acetonitrile (3×10 ml) and dried under vacuum (1.85 g, 82%).

The product was characterized on the basis of the following data: $^1$H NMR (C$_6$D$_6$, 500.1 MHz): 7.18–7.15 (m, 4 H, o—,m.—C$_6$H$_5$), 6.87 (t, 1 H, p—C$_6$H$_5$, J=Hz), 3.02 (s, 2 H, CH$_2$Ph), 1.99–1.13 (m, 63 H, c—C$_5$H$_9$). $^{13}$C NMR (C$_6$D$_6$, 125.8 MHz): 142.90 (s, ipso-Ph), 124.34 (s, Ph, other signals obscured by solvent), 81.53 (CH$_2$Ph), 27.92, 27.90, 27.87, 27.78, 27.46 (s, CH$_2$), 22.73, 22.65, 22.40 (s, 3:1:3 for CH). $^{29}$Si NMR (C$_6$D$_6$, 99.4 MHz): −62.72, −64.74, −65.88 (s, 3:1:3). Anal. Calcd for C$_{42}$H$_{70}$O$_{12}$Si$_7$Ti (found): C, 49.87 (−); H, 6.98 (6.80).

2.4=Ti(O$^i$Pr){(c—C$_5$H$_9$)$_7$Si$_7$O$_{12}$}

[Ti(O$^i$Pr)$_4$] (0.48 g, 1.69 mmol) was added via syringe to a vigorously stirred suspension of (c—C$_5$H$_9$)$_7$Si$_7$O$_9$(OH)$_3$ (1.350 g, 1.54 mmol) in diethyl ether (120 ml). The mixture was stirred at room temperature for 4 h, after which time work-up (as described above) afforded Ti(OiPr){(c—C$_5$H$_9$)7Si$_7$O$_{12}$} as a white solid (1.291 g, 85%).

The product was characterized on the basis of the following data: $^1$H NMR (C$_6$D$_6$, 500.1 MHz): 4.40 (septet, 1 H, CH(CH$_3$)$_2$, J=6.0 Hz), 1.94–1.11 (m, 63 H, c—C$_5$H$_9$), 1.18 (d, 6 H, CH(CH$_3$)$_2$, J=6.0 Hz). $^{13}$C NMR (C$_6$D$_6$, 100.6 MHz): 80.09 (s, CH(CH$_3$)$_2$), 28.05, 27.97, 27.87, 27.51, 27.44 (s, CH$_2$), 25.67 (s, CH$_3$), 22.84, 22.77, 22.64 (s, 3:1:3 for CH). $^{29}$Si NMR (C$_6$D$_6$, 79.5 MHz): −63.81, −65.80, −66.83 (s, 3:1:3). Anal. Calcd for C$_{38}$H$_{70}$O$_{13}$Si$_7$Ti (found): C, 46.60 (45.79); H, 7.20 (6.96).

2.5=Ti(p—OC$_6$H$_4$NO$_2$){(c—C$_5$H$_9$)$_7$Si$_7$O$_{12}$}

A solution of p—HOC$_6$H$_4$NO$_2$ (0.097 g, 0.70 mmol) in diethyl ether (20 ml) was added dropwise via syringe to a vigorously stirred slurry of Ti(CH$_2$Ph){(c—C$_5$H$_9$)$_7$Si$_7$O$_{12}$} (0.702 g, 0.69 mmol) in diethyl ether (40 ml) cooled to −30° C. After stirring at this temperature for 1 h the mixture was allowed to warm slowly to room temperature and stirred for a further 2 h, after which time work-up (as described above) afforded Ti(p—OC$_6$H$_4$NO$_2$){(c—C$_5$H$_9$)$_7$Si$_7$O$_{12}$} as a yellow solid (0.257 g, 35%).

2.6=Ti(p—OC$_6$H$_4$NO$_2$){(c—C$_6$H$_{11}$)$_7$Si$_7$O$_{12}$}

Reaction of p—HOC$_6$H$_4$NO$_2$ with Ti(CH$_2$Ph){(c—C$_6$H$_{11}$)$_7$Si$_7$O$_{12}$} using the procedure described for 2.5, afforded Ti(p—OC$_6$H$_4$NO$_2$){(c—C$_6$H$_{11}$)$_7$Si$_7$O$_{12}$} as a yellow solid in 48% yield.

2.7=Ti(OSiMe$_3$){(c—C$_6$H$_{11}$)$_7$Si$_7$O$_{12}$}

Addition of [Ti(OSiMe$_3$)$_4$] (1.08 g, 2.67 mmol) to a slurry of (c—C$_6$H$_{11}$)$_7$Si$_7$O$_9$(OH)$_3$ (2.595 g, 2.67 mmol) in diethyl ether (50 ml), followed by work-up as above, afforded a white microcrystalline solid (2.817 g, 95%).

The product was characterized on the basis of the following data: $^1$H NMR (C$_6$D$_6$, 250.1 MHz): δ2.13–0.97 (m, 77 H, c—C$_6$H$_{11}$), 0.21 (s, 9 H, SiMe$_3$). $^{13}$C NMR (C$_6$D$_6$, 100.6 MHz): 827.80, 27.76, 27.42, 27.40, 27.32, 27.25, 27.18 (s, CH$_2$), 23.88, 23.85, 23.61 (s, 3:1:3 for CH), 1.59 (s, SiMe$_3$). $^{29}$Si NMR (C$_6$D$_6$, 79.5 MHz): δ−65.80, −67.90, −68.85 (s, 3:1:3). Anal. Calcd for C$_{45}$H$_{86}$O$_{13}$Si$_8$Ti (found): C, 48.79 (48.56); H, 7.82 (7.69).

2.8=Ti(O$^i$Pr){(c—C$_6$H$_{11}$)$_7$Si$_7$O$_{12}$}, 10 wt % immobilized on silylated silica Silylated silicagel was prepared by passing hexamethyldisilazane, Me$_3$Si)$_2$SiNH, over a bed of silicagel heated to 180° C. for two hours, using dry nitrogen as the carrier gas. Excess hexamethyldisilazane was stripped with nitrogen. After cooling to room temperature, 10.0 g of the silylated material was transferred to a flask, to which a solution of 2.2 (1.01 g, 0.94 mmol) in toluene (8.0 ml) was added dropwise via syringe, with vigorous shaking of the flask. The volume of toluene employed was chosen so as to approximately equal the total pore volume (0.8 ml/g) of the silylated silica. After addition of the solution was complete, the flask was sealed and placed on a roller-bank for a period of 1 h. Finally, the solid was dried under vacuum (1 Pa).

EXAMPLE 3
Preparation of Oxiranes

Catalysts 2.1–2.8 according to the invention were compared with Comparative Catalysts A and B. Comparative Catalyst A is a commercial heterogeneous (titania on silylated silica) catalyst according to EP-B-345856. Comparative Catalyst B, molybdenyl acetylacetate MoO$_2$(acac)$_2$ purchased from Aldrich Co, is a known homogeneous epoxidation catalyst, as disclosed in the Coleman-Kammula and Duim-Koolstra publication.

In these experiments 3.1 and 3.2, the activity of the tested catalysts was expressed in a comparative manner by their second order reaction rate constant k$_2$, based on the hydroperoxide (TBHP) conversion per unit of time.

When the olefin reactant is used at stoichiometric excess (such as in these experiments) the reaction kinetics follow a pseudo-first order pattern corresponding to the rate equation:

rate=d[epoxide]/dt=k$_1$[hydroperoxide], wherein k$_1$=k$_2$[Ti], [Ti] being the concentration of the titanasilsesquioxane catalysts in moles per liter.

Standard rate plots of −ln[hydroperoxide] versus l/t then afford straight lines with slope k$^1$, from which the second order rate constant k$_2$, expressed in M$^{-1}$s$^{-1}$, can be calculated: k$_2$=k$_1$/[Ti].

The per cent selectivity to the desired epoxide product (mol 1,2-epoxyoctane and propylene oxide, respectively, formed per mol TBHP consumed) was also determined in experiments 3.1 and 3.2.

3.1=1-octene epoxidation using tert-butyl hydroperoxide (TBHP)

In experiments 3.1.1–3.1.7, toluene (3 g, 0.03 mol as internal standard for GLC analysis), 1-octene (73 g, 0.6 mol) and a stirrer bar were place in a nitrogen-filled 250 ml three neck flask, equipped with a condenser, a thermometer probe and a septum. The mixture was warmed to 80° C. and TBHP (30 mmol, 3M solution in iso-octane) was added via a syringe, followed by a solution of the titanasilsesquioxane (equivalent to 0.2 mmol) dissolved in octane (10 ml), or preceded by the heterogeneous catalyst in solid form.

In experiments 3.1.9–3.1.10 the same set-up was used, the catalyst being respectively Comparative Catalyst A and Comparative Catalyst B. The amount of Comp. cat. B used in experiment 3.1.10 was 0.2 mmol.

Experiment 3.1.8, using the silica supported titanasilsesquioxane catalyst 2.8, differed in that the amount of 1-octene reactant was 18.25 g (0.15 mol) and 100 ml of acetonitrile was added as a separate solvent.

Immediately at the start of the reaction, and at regular intervals thereafter, a sample was taken for analysis by Gas Liquid Chromatography (GLC) and iodometric titration.

GLC analyses were performed on a Hewlett-Packard HP 5890 instrument, with flame ionization detection (FID), a 25 m×0.32 mm (0.52 m film thickness) HP-1 (cross-linked methyl silicone gum) fused silica capillary column, and helium as carrier gas. TBHP was determined by iodometric titration with sodium thiosulphate.

The results are presented in the following Table 1.

TABLE 1

Epoxidation of 1-octene with TBHP

| Exp. | Catalyst | $k_2$ $(M^{-1}s^{-1})$ | Reaction Time (min.) | Conversion of TBHP (%) | Selectivity to epoxide (%) |
|---|---|---|---|---|---|
| 3.1.1 | 2.1 | 1.360 | 0 | 0 | — |
|  |  |  | 5 | 49 | 92 |
|  |  |  | 10 | 78 | 94 |
|  |  |  | 15 | 87 | 91 |
|  |  |  | 20 | 93 | 94 |
|  |  |  | 30 | 100 | 90 |
|  |  |  | 60 | 100 | 97 |
| 3.1.2 | 2.2 | 1.360 | 0 | 0 | — |
|  |  |  | 5 | 52 | 89 |
|  |  |  | 10 | 75 | 90 |
|  |  |  | 15 | 86 | 90 |
|  |  |  | 20 | 92 | 90 |
|  |  |  | 30 | 97 | 90 |
|  |  |  | 60 | 100 | 90 |
| 3.1.3 | 2.3 | 1.980 | 0 | 0 | — |
|  |  |  | 5 | 64 | 86 |
|  |  |  | 10 | 87 | 87 |
|  |  |  | 15 | 94 | 87 |
|  |  |  | 20 | 98 | 88 |
|  |  |  | 30 | 100 | 87 |
|  |  |  | 60 | 100 | 88 |
| 3.1.4 | 2.4 | 2.740 | 0 | 0 | — |
|  |  |  | 5 | 77 | 86 |
|  |  |  | 10 | 93 | 86 |
|  |  |  | 15 | 100 | 84 |
|  |  |  | 20 | 100 | 86 |
|  |  |  | 30 | 100 | 87 |
|  |  |  | 60 | 100 | 86 |
| 3.1.5 | 2.5 | 1.420 | 0 | 0 | — |
|  |  |  | 5 | 48 | 89 |
|  |  |  | 10 | 75 | 88 |
|  |  |  | 15 | 88 | 87 |
|  |  |  | 20 | 83 | 91 |
|  |  |  | 30 | 98 | 90 |
|  |  |  | 60 | 100 | 89 |
| 3.1.6 | 2.6 | 1.130 | 0 | 0 | — |
|  |  |  | 5 | 36 | 100 |
|  |  |  | 10 | 61 | 99 |
|  |  |  | 15 | 77 | 94 |
|  |  |  | 20 | 86 | 94 |
|  |  |  | 30 | 94 | 96 |
|  |  |  | 60 | 100 | 94 |
| 3.1.7 | 2.7 | 0.940 | 0 | 0 | — |
|  |  |  | 5 | 37 | 94 |
|  |  |  | 10 | 62 | 95 |
|  |  |  | 15 | 75 | 95 |
|  |  |  | 20 | 84 | 96 |
|  |  |  | 30 | 93 | 95 |
|  |  |  | 60 | 100 | 94 |
| 3.1.8 | 2.8 | 0.264 | 0 | 0 | — |
|  |  |  | 10 | 22 | 86 |
|  |  |  | 20 | 33 | 89 |
|  |  |  | 35 | 39 | 95 |
|  |  |  | 60 | 58 | 89 |
| 3.1.9 | Comp. A | 0.183 | 0 | 0 | — |
|  |  |  | 15 | 19 | 96 |
|  |  |  | 30 | 36 | 82 |
|  |  |  | 60 | 57 | 98 |
| 3.1.10 | Comp. B | 0.310 | 0 | 0 | — |
|  |  |  | 10 | 4 | 65 |
|  |  |  | 15 | 11 | 87 |
|  |  |  | 20 | 22 | 84 |
|  |  |  | 30 | 44 | 88 |
|  |  |  | 45 | 66 | 91 |
|  |  |  | 60 | 79 | 92 |

3.2 = propene epoxidation using tert-butyl hydroperoxide (TBHP)

A nitrogen-filled 500 ml stainless steel autoclave was charged with toluene (100 ml), TBHP (50 mmol, 3M solution in iso-octane), propene (16 g, 0.38 mol) and nonane (3 ml, 17 mmol as internal standard for GLC analysis). The autoclave was sealed and the temperature raised to 80° C. The reaction was started by injecting the catalyst solution (0.1 mmol catalyst dissolved in 12 ml toluene) into the autoclave. Immediately at the start of the reaction, and at regular intervals thereafter, a sample was taken for analysis (GLC and iodometric titration), which was performed as described in 3.1.

The results are presented in the following Table 2.

TABLE 2

Epoxidation of propene with TBHP

| Exp. | Catalyst | $k_2$ $(M^{-1}s^{-1})$ | Reaction Time (min.) | Conversion of TBHP (%) | Selectivity to epoxide (%) |
|---|---|---|---|---|---|
| 3.2.1 | Comp. A | 0.118 | 0 | 0 | — |
|  |  |  | 13 | 7 | 45 |
|  |  |  | 23 | 12 | 50 |
|  |  |  | 43 | 19 | 55 |
|  |  |  | 73 | 30 | 62 |
| 3.2.2 | 2.2 | 0.248 | 0 | 0 | — |
|  |  |  | 10 | 10 | 91 |
|  |  |  | 30 | 27 | 84 |
|  |  |  | 60 | 49 | 83 |
| 3.2.3 | 2.3 | 0.408 | 0 | 0 | — |
|  |  |  | 10 | 20 | 77 |
|  |  |  | 30 | 46 | 70 |
|  |  |  | 60 | 66 | 73 |

We claim:

1. A process for the preparation of an oxirane compound by reacting an olefinically unsaturated hydrocarbon with an organic hydroperoxide, in the presence of a catalyst comprising a titanasilsesquioxane of the general formula $TiLR_7Si_7O_{12}$ and the structural formula

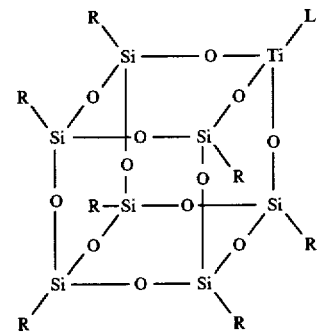

wherein R is chosen from the group of cyclopentyl, cyclohexyl and cycloheptyl and L is chosen from the group of alkyl, cycloalkyl, alkylaryl, alkoxy, aryloxy, siloxy, amido and OH.

2. Process according to claim 1, characterized in that L is chosen from the group of phenoxy, isopropoxy, benzyl, trimethylsiloxy and dimethyl amido.

3. Process according to claim 1, characterized in that the titanasilsesquioxane is supported on an inert inorganic carrier material having a specific surface area of at least 10 m² per gram and a pore volume of at least 0.1 ml per gram.

4. Process according to claim 3, characterized in that the carrier material is chosen from the group of silylated silica, silicon carbide and activated coal.

5. Process according to claim 1, characterized in that it is performed in a homogeneous reaction system and the amount of titanasilsesquioxane used is in the range of from $10^{-3}$ to $10^{-5}$ mol of titanium (calculated as the oxide) per mol of the organic hydroperoxide to be reacted.

6. Process according to claim 1, characterized in that the olefinically unsaturated hydrocarbon is selected from the group of propylene, butylene, isobutylene, butadiene, hexene-3, octene-1 and decene-1.

7. Process according to claim 1, characterized in that the organic hydroperoxide is selected from the group of ethylbenzene hydroperoxide, cumene hydroperoxide and tertiary butyl hydroperoxide.

8. Process according to claim 1, characterized in that the reaction is performed in the liquid phase, at a temperature in the range of from 0° to 200° C. and at a pressure of from 100 to 10000 kPa.

9. Process according to claim 5, characterized in that the olefinically unsaturated hydrocarbon is selected from the group of propylene, butylene, isobutylene, butadiene, hexene-3, octene-1 and decene-1.

10. Process according to claim 9, characterized in that the organic hydroperoxide is selected from the group consisting of ethylbenzene hydroperoxide, cumene hydroperoxide and tertiary butyl hydroperoxide.

11. Process according to claim 10, characterized in that the reaction is performed in the liquid phase, at a temperature in the range of from 0° to 200° C. and at a pressure of from 100 to 10000 kPa.

* * * * *